United States Patent [19]
Franzel et al.

[11] Patent Number: 5,782,817
[45] Date of Patent: Jul. 21, 1998

[54] CATHETER INTRODUCER HAVING TOROIDAL VALVE

[75] Inventors: Raymond C. Franzel; Roberta D. Goode, both of Miami, Fla.

[73] Assignee: Cordis Corporation, Miami Lakes, Fla.

[21] Appl. No.: 554,096

[22] Filed: Nov. 6, 1995

[51] Int. Cl.[6] ............................... A61M 5/00
[52] U.S. Cl. ................... 604/256; 604/167; 251/5
[58] Field of Search ....................... 604/167, 169, 604/246, 250, 256, 264; 606/184, 185; 251/149.2, 149.6, 149.1, 4, 5, 11

[56] References Cited

U.S. PATENT DOCUMENTS

| | | |
|---|---|---|
| 4,000,739 | 1/1977 | Stevens . |
| 4,303,100 | 12/1981 | Kalb ........................... 137/853 |
| 4,421,296 | 12/1983 | Stephens . |
| 4,626,245 | 12/1986 | Weinstein . |
| 4,783,045 | 11/1988 | Tartaglino ..................... 251/61.1 |
| 4,895,565 | 1/1990 | Hillstead . |
| 5,207,656 | 5/1993 | Kranys . |
| 5,360,417 | 11/1994 | Gravener et al. ............... 604/278 |
| 5,366,478 | 11/1994 | Brinkerjoff et al. ............ 606/213 |
| 5,429,609 | 7/1995 | Yoon ............................ 604/167 |
| 5,460,616 | 10/1995 | Weinstein et al. .............. 604/167 |
| 5,634,937 | 6/1997 | Mollenauer et al. ............ 606/213 |

*Primary Examiner*—Corrine M. McDermott
*Attorney, Agent, or Firm*—Gerstman, Ellis & McMillin, Ltd.

[57] ABSTRACT

A catheter introducer defines a tubular sheath with a housing on one end thereof, with the housing enclosing a fluid-filled, elastic-walled toroidal member defining a central aperture aligned with the tubular sheath axis. The central aperture is normally closed, being retained in the closed position by an elastic sleeve carried by the toroidal member. The central aperture is penetrable by a catheter in sealing manner as the catheter is advanced through the catheter sheath introducer.

10 Claims, 1 Drawing Sheet

5,782,817

CATHETER INTRODUCER HAVING TOROIDAL VALVE

BACKGROUND OF THE INVENTION

Catheter introducers are a well known form of catheter, used to assist in the introduction of other catheters and guidewires to the arteriovenous system of a patient. Such catheter introducers comprise a tubular sheath or cannula having a housing carried on one end thereof, with the housing enclosing a hemostasis valve. Examples of such catheter introducers are numerous, with some being disclosed in Stevens U.S. Pat. Nos. 4,000,739 and 4,421,296. Other examples of catheter introducers are disclosed in Kranys U.S. Pat. No. 5,207,656; Weinstein U.S. Pat. No. 4,626,245; and Hillstead U.S. Pat. No. 4,895,565.

In the devices of the above described patents, the hemostasis valve comprises a flat, elastic partition seal with a center cut, either an aperture or a slit, through which a catheter (or guidewire) passes as it extends through the catheter introducer. These flat seals must be capable of allowing passage of catheters while maintaining sufficient elasticity to snap closed after removal thereof.

By this invention, a valve for a catheter introducer is provided which uses internal radial pressure around an aperture which does not exhibit slits or cuts. This eliminates possible tearing of the slits or cuts as a catheter is pushed through the valve. It also eliminates the manufacturing operation of cutting the slits.

DESCRIPTION OF THE INVENTION

By this invention, a catheter introducer comprises a tubular sheath having a housing carried on one end thereof. The housing encloses a fluid-filled, elastic-walled toroidal member defining a central aperture aligned with the tubular sheath axis. The central aperture is normally closed to provide sealing, but is penetrable by a catheter or the like while maintaining a sealing relationship as the catheter is advanced through the catheter introducer.

Thus, the toroidal member in the housing serves as a hemostasis valve, preventing back-flow of blood, as is desired for catheter introducers. Furthermore, no slits are required to be cut in a partition, with the advantages described above.

The toroidal member may be filled with a compressible fluid, which may be air, optionally in the form of bubbles of a closed-cell foam, or otherwise as a toroidal chamber within an elastomeric wall. The normally-closed, central aperture is preferably surrounded by an elastic ring carried by the toroidal member, to provide biasing force of the central aperture into its normally closed position. Typically, the elastic ring may be positioned within the wall of the toroidal member, being protected from frictional contact with catheters or guidewires as they advance or retract through the catheter introducer, for better maintenance of its elastic properties. However, the elastic ring may define the central aperture, with the toroidal member being positioned and sealed to the outer surface of the elastic ring, if desired.

Thus, the valve of this invention for a catheter introducer operates rather like a sphincter, having a soft, deformable, donut-shaped or toroidal pouch with a small, normally closed central aperture in its center. As a catheter or other elongated member is passed through the central aperture of the toroidal valve, the elastic ring and the toroidal member are urged to fit the contours of the catheter or other device. Because the ring and the toroidal member can follow the contours of the catheter closely, back bleeding around the catheter is minimized.

Upon removal of the device, the valve opening of the central aperture closes under inward radial pressure from the inner elastic ring and typically also the compressible fluid in the toroidal member, although the toroidal member may be open to the exterior to always be at ambient pressure, if desired.

Also, an external lubricant such as silicone oil may be applied to the valve, and particularly the area of the central aperture.

DESCRIPTION OF SPECIFIC EMBODIMENTS

Figure 1:
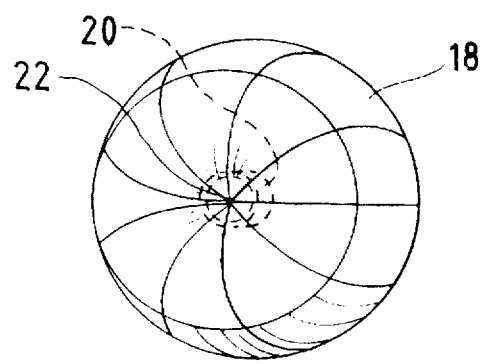
FIG. 1 is a perspective view of the toroidal member which is carried in the housing of the catheter introducer of this invention.

Referring to the drawings, a catheter introducer 10 is disclosed, comprising a tubular sheath 12 having a housing 14 carried on one end thereof. Except as otherwise shown, catheter introducer 10 may be of conventional design.

Figure 2:
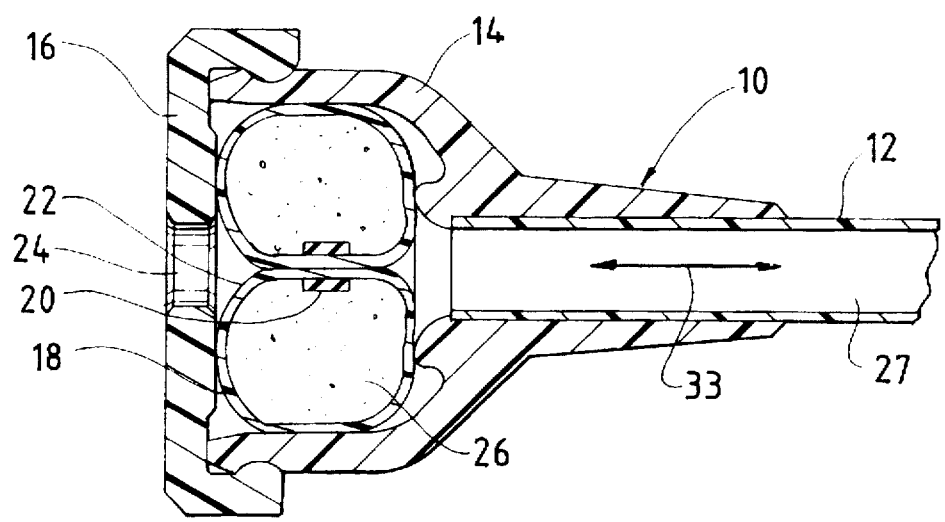
FIG. 2 is a longitudinal sectional view of the proximal portion of a catheter introducer, carrying the toroidal member of FIG. 1.

Housing 14 is closed by end cap 16 as shown, and contains toroidal member 18 in the housing interior. Toroidal member 18 comprises a flexible plastic, toroidal outer wall as shown, with a flexible, elastic sleeve 20 in its interior which is preferably somewhat radially outwardly stretched as shown in FIG. 2 so that, as sleeve 20 urges toward its natural, unstressed position, the central toroidal aperture 22 is normally closed.

The remainder of catheter introducer 10 may be entirely conventional. For example, housing 14 may carry a side port in conventional manner to facilitate flushing of the device.

Cap 16 may fit on housing 14 with a snap-fit arrangement as shown, or it may be sealed in place. Cap 16 defines a central aperture 24 for access by a catheter or the like which is to be passed through introducer 10.

Toroidal member 18 may be filled, preferably with a compressible fluid such as air 26 or a flexible foam. However member 18 may be solid if made of a soft rubber.

Catheter sheath introducer 10 may be emplaced in an artery of the patient for angiography or angioplasty, as needed. This is conventionally accomplished by placing a conventional dilator stylette through the bore 27 of sheath 12, extending through the toroidal aperture 22. Then, as the dilator is removed, bore 27 of sheath 12 is exposed to blood and arterial pressure, causing a backflow of blood through sheath 12 to the toroidal valve 18 and elastic sleeve 20. There, the backflow of blood is stopped by the valving action of the toroidal valve, which is made of member 18 and sleeve 20.

Figure 3:
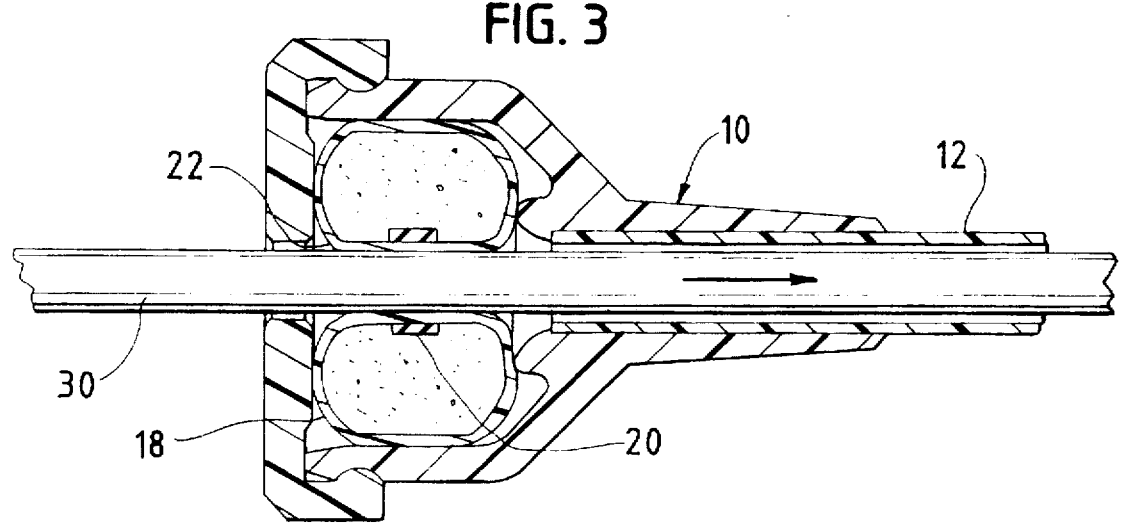
FIG. 3 is a longitudinal sectional view similar to FIG. 2, showing a catheter being inserted through the catheter introducer.

FIG. 3 shows the proximal end of the same catheter introducer 10 as is shown in FIG. 2, but with a catheter 30 extending through central aperture 22, outwardly stretching elastic sleeve 18 and toroidal valve 18. Catheter 30 may thus be advanced or retracted through catheter introducer 10 into and out of the arteriovenous system of a patient, while minimizing injury to the patient's tissue at the access site because of the presence of introducer 10. Sheath 20 and toroidal member 18 provide a compressive seal around catheter 30, which prevents the leakage of pressurized blood proximally outwardly, while catheter 30 can be advanced or retracted as required.

If desired, toroidal member 18 may be provided by itself without sleeve 20, particularly if member 18 has a pressurized interior, so as to provide a pressure seal closing off central aperture 22 in its own right, while still being compressible enough so that toroidal member 18 can expand to sealingly receive a catheter similar to catheter 30 in sliding relation as shown.

Elastic sleeve 18 preferably has a length that is about ⅛ to ½ the length of toroidal member 18, each of the above lengths being measured parallel to the longitudinal axis 33 of catheter 12. This facilitates the low friction of catheters in the valve.

The above has been offered for illustrative purposes only, and is not intended to limit the scope of the invention of this application, which is as defined in the claims below.

That which is claimed is:

1. A catheter introducer which comprises a tubular sheath having an axis and a housing carried on one end thereof, said housing enclosing a flexible-walled toroidal member defining a central aperture aligned with the tubular sheath axis, said central aperture being normally closed but penetrable by a catheter in sealing manner as the catheter is advanced through said catheter sheath introducer, said normally closed central aperture being surrounded by an elastic sleeve carried by said toroidal member to bias said central aperture into closed position.

2. The catheter sheath introducer of claim 1 in which said toroidal member is filled with a compressible fluid.

3. The catheter sheath introducer of claim 2 in which said elastic sleeve is positioned within the wall of said toroidal member.

4. The catheter sheath introducer of claim 1 in which said elastic sleeve is positioned within the wall of said toroidal member.

5. The catheter sheath introducer of claim 1 in which said elastic sleeve has a length that is from ⅛ to ½ the length of said toroidal member.

6. A catheter introducer which comprises a tubular sheath having a housing carried on one end thereof, said housing enclosing an elastic-walled toroidal member which is filled with a compressible fluid, said toroidal member defining a central aperture aligned with the tubular sheath axis, said central aperture being normally closed, said normally closed central aperture being surrounded by an elastic sleeve carried by said toroidal member to bias the central aperture into closed position, said central aperture being penetrable by a catheter in sealing manner with stretching of said elastic sleeve as the catheter is advanced through the catheter sheath introducer.

7. The catheter sheath introducer of claim 6 in which said elastic sleeve is positioned within the wall of said toroidal member.

8. The catheter sheath introducer of claim 7 in which said compressible fluid of the toroidal member is air.

9. The catheter sheath introducer of claim 7 in which said elastic sleeve has a length that is from ⅛ to ½ the length of said toroidal member.

10. The catheter sheath introducer of claim 6 in which said compressible fluid of the toroidal member is air.

* * * * *